United States Patent
Deeley et al.

(10) Patent No.: US 11,384,302 B2
(45) Date of Patent: Jul. 12, 2022

(54) METHODS FOR PREPARING FUEL ADDITIVES

(71) Applicant: BP OIL INTERNATIONAL LIMITED, Middlesex (GB)

(72) Inventors: Jon Michael Stewart Deeley, Hull (GB); Sorin Vasile Filip, Reading (GB); Gregory Price, Hull (GB)

(73) Assignee: BP OIL INTERNATIONAL LIMITED, London (GB)

( * ) Notice: Subject to any disclaimer, the term of this patent is extended or adjusted under 35 U.S.C. 154(b) by 10 days.

(21) Appl. No.: 16/958,732

(22) PCT Filed: Dec. 19, 2018

(86) PCT No.: PCT/EP2018/086027
§ 371 (c)(1),
(2) Date: Jun. 28, 2020

(87) PCT Pub. No.: WO2019/129592
PCT Pub. Date: Jul. 4, 2019

(65) Prior Publication Data
US 2020/0332210 A1     Oct. 22, 2020

(30) Foreign Application Priority Data
Dec. 27, 2017   (GB) ..................... 1721967

(51) Int. Cl.
| | | |
|---|---|---|
| *C10L 1/223* | (2006.01) | |
| *C10L 1/233* | (2006.01) | |
| *C07D 265/36* | (2006.01) | |
| *C10L 10/10* | (2006.01) | |

(52) U.S. Cl.
CPC ............ *C10L 1/233* (2013.01); *C07D 265/36* (2013.01); *C10L 10/10* (2013.01); *C10L 2270/023* (2013.01); *C10L 2290/24* (2013.01)

(58) Field of Classification Search
CPC .... C10L 1/233; C10L 10/10; C10L 2270/023; C10L 2290/24; C07D 265/36
See application file for complete search history.

(56) References Cited

U.S. PATENT DOCUMENTS

| | | | |
|---|---|---|---|
| 4,288,589 | A | 9/1981 | Loew et al. |
| 4,861,914 | A | 8/1989 | Weidig et al. |
| 8,222,417 | B2 | 7/2012 | Suzuki et al. |
| 2005/0261244 | A1 | 11/2005 | Tuerdi et al. |
| 2006/0123696 | A1 | 6/2006 | Gaughan et al. |
| 2008/0064871 | A1 | 3/2008 | Hirata et al. |
| 2009/0094887 | A1 | 4/2009 | Calvert et al. |

FOREIGN PATENT DOCUMENTS

| | | | |
|---|---|---|---|
| CN | 105272904 | A | 4/2019 |
| EP | 2172453 | A1 | 4/2010 |
| EP | 3205701 | A1 | 8/2017 |
| EP | 3205703 | A1 | 8/2017 |
| GB | 1013572 | * | 12/1965 |
| GB | 2026524 | A | 2/1980 |
| JP | H04247017 | A | 9/1992 |
| KR | 20120102381 | A | 9/2012 |
| WO | 2009001817 | A1 | 12/2008 |
| WO | 2011048112 | A1 | 4/2011 |
| WO | 2011103460 | A1 | 8/2011 |
| WO | 2012009678 | A1 | 1/2012 |
| WO | 2014047390 | A1 | 3/2014 |
| WO | 2015063694 | A1 | 5/2015 |
| WO | 2017108723 | A2 | 6/2017 |
| WO | 2017137518 | A1 | 8/2017 |

(Continued)

OTHER PUBLICATIONS

Shadyro, O.I. et al. "Synthesis and Antiviral Activity of N-Acyl Derivatives of 4,6-Di-(tert-butyl)-2-aminophenol." Pharmaceutical Chemistry Journal. 2002, 36(8), p. 410-412.
Perry, B. et al. "Achieving multi-isofrom-PI3K inhibition in a series of substituted 3,4-dihydro-2H-benzo[1,4] oxazines." Bioorg Med Chem Lett. 2008, 18, 16, p. 4700-4704.
Dugar, S. et al. "A Concise and Efficient Synthesis of Substituted Morpholines." Synthesis. 2014, 47, 5, p. 712-720.
International Search Report and Written Opinion of International Application No. PCT/EP2018/086022, dated Apr. 10, 2019.

(Continued)

*Primary Examiner* — Cephia D Toomer
(74) *Attorney, Agent, or Firm* — McDonnell Boehnen Hulbert & Berghoff LLP

(57) ABSTRACT

A method for preparing a fuel additive d is provided. The method comprises carrying out the following reaction: (1) The fuel additive d may be used as an octane-boosting additive in a fuel for a spark, ignition internal combustion engine.

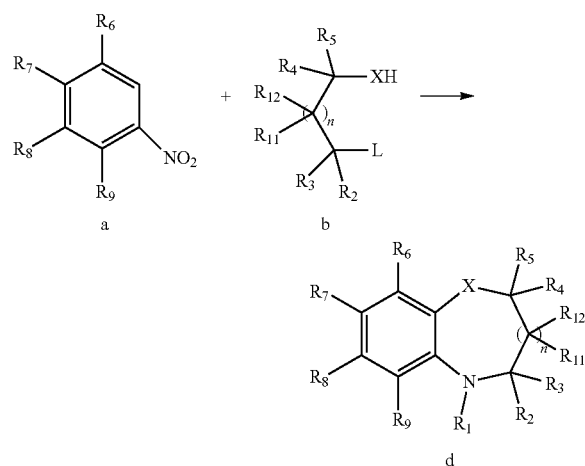

18 Claims, No Drawings

(56) References Cited

FOREIGN PATENT DOCUMENTS

WO 2017142833 A1 8/2017

OTHER PUBLICATIONS

Coudert, G. et al. "A new synthesis of 3,4-dihydro-2H-1,4-benzoxazines using solid-liquid phase-transfer catalysis." Synthesis Georg Thieme Verlag. 1979, 7, p. 541-543.
Kotha, S. "Synthesis and Reactions of 3,4-dihydro-2H-1,4-benzoxazine Derivatives." Heterocycles. 1994, 38, p. 5-8.
Hernandez-Olmos, V. et al. "N-Substituted Phenoxazine and Acridone Derivatives: Structure-Activity Relationships of Potent P2X4 Receptor Antagonists." J. Med. Chem. 2012, 55, 22, p. 9576-9588.
Bunce, R.A. et al. "Tetrahydro-1,5-benzoxazepines and tetrahydro-1H-1,5-benzodiazepines by a tandem reduction-reductive amination reaction." J. Heterocyclic Chem. 2004, 41, 6, p. 963-970.
Shadyro, O.I. et al. "Synthesis and Antiviral Activity of N-Acyl Derivatives of 4,6-Di-(tert-butyl)-2-aminophenol." Pharmaceutical Chemistry Journal 2003, 37, p. 399-401.
International Search Report and Written Opinion for International Application No. PCT/EP2018/086023, dated Jul. 4, 2019.
International Search Report and Written Opinion for International Application No. PCT/EP2018/086027, dated May 10, 2019.
Filippou, P.S. et al. "Regulation of the *Escherichia coli* AtoSC two component system by synthetic biologically active 5;7;8-trimethyl-1;4-benzoxazine analogues." Bioorgan Med Chem. 2011, 19, 16, p. 5061-5070.
Ramesh, C. et al. "A simple and facile route for the synthesis of 2H-1,4-benzoxazin-3-(4H)-ones via reductive cyclization of 2-(2-nitrophenoxy)acetonitrile adducts in the presence of Fe/acetic acid." Tetrahedron. 2011, 67, 6, p. 1187-1192.
Reddy, Ch. R. et al. "Reductive N-alkylation of aromatic amines and nitro compounds with nitriles using polymethylhydrosiloxane." Tetrahedron Let. 2007, 48, 15, p. 2765-2768.
International Search Report and Written Opinion for International Application No. PCT/EP2018/086025, dated Jun. 6, 2019.
Bartsch, H. et al. "Synthese und Reaktivität von 2- und 3-hydroxylierten Dihydro-1,4-Benzoxazinen." Monatshefte für Chemie. 1997, 110, p. 267-278.
Mizar, P. et al. "Synthesis of substituted 4-(3-alkyl-1,2,4-oxadiazol-5-ylmethyl)-3,4-dihydro-2H-1,4-benzoxazines and 4-(1H-benzimidazol-2-ylmethyl)-3,4-dihydro-2H-1,4-benzoxazines." Tetrahedron Let. 2006, 47, 44, p. 7823-7826.
Fu, Y. et al. "Simple and efficient synthesis of novel N-dichloroacetyl-3,4-dihydro-2H-1,4-benzoxazines." Heterocycl Commun. 2012, 18, 3, p. 143-146.
International Search Report and Written Opinion for International Application No. PCT/EP2018/086024, dated Jun. 6, 2019.
Knorr, L. "Synthesen in der »Oxazinreihe«." Ber. Dtsch. Chem. Ges. 1889, 22, p. 2081-2099.
Calderone, V. et al "Structural modifications of benzanilide derivatives, effective potassium channel openers. X." Eur. J. Med. Chem. 2006, 41(12), p. 1421-1429.
Liu, Y. et al. "Concise synthesis of 3,4-dihydro-1,4-benzoxazines by three-component reactions of acyl chlorides, o-aminophenols and 1,2-dichloroethane." Tetrahedron 2018, 74(27), p. 3691-3696.
Huerta, G. et al. "Facile Synthesis of Aminoalcohols by Ring Opening of Epoxides Under Solvent Free Conditions." Synthetic Commun. 2004, 34(13), p. 2393-2406.
Woydowski, K. "Optically Active Heterocycles through Ring Transformations on Oxirane3-carboxylate Derivatives." Sel. Org. React. Database (SORD). 1999. See CASREACT abstract accession No. 161 :698073.
Gao, S. et al. "Synthesis and crystal structure of N-dichloroacetyl-3,4-dihydro-3-methyl-6-chloro-2H-1,4-benzoxazine". Journal of Chemistry. 2015, 2015, Article ID 268306, p. 1-5.
Yang, J. et al. "Synthesis, anti-cancer evaluation of benzenesulfoamide derivates as potent tubulin-targeting agents." Eur. J. Med. Chem. 2016, 122, p. 488-496.

\* cited by examiner

METHODS FOR PREPARING FUEL ADDITIVES

This application is a national stage application under 35 U.S.C. § 371 of International Application No. PCT/EP2018/086027, filed Dec. 19, 2018, which claims priority to Great Britain Application No. 1721967.6, filed Dec. 27, 2017, the disclosures of which are explicitly incorporated by reference herein.

FIELD OF THE INVENTION

This invention relates to methods for preparing octane-boosting additives for use in a fuel for a spark-ignition internal combustion engine. In particular, the invention relates to methods for preparing octane-boosting additives that are derivatives of benzo[1,4]oxazines and 1,5-benzoxazepines. The invention further relates to methods for preparing fuels for a spark-ignition internal combustion engine comprising the octane-boosting additives.

BACKGROUND OF THE INVENTION

Spark-ignition internal combustion engines are widely used for power, both domestically and in industry. For instance, spark-ignition internal combustion engines are commonly used to power vehicles, such as passenger cars, in the automotive industry.

Fuels for a spark-ignition internal combustion engine (generally gasoline fuels) typically contain a number of additives to improve the properties of the fuel.

One class of fuel additives is octane improving additives. These additives increase the octane number of the fuel which is desirable for combatting problems associated with pre-ignition, such as knocking. Additisation of a fuel with an octane improver may be carried out by refineries or other suppliers, e.g. fuel terminals or bulk fuel blenders, so that the fuel meets applicable fuel specifications when the base fuel octane number is otherwise too low.

Organometallic compounds, comprising e.g. iron, lead or manganese, are well-known octane improvers, with tetraethyl lead (TEL) having been extensively used as a highly effective octane improver. However, TEL and other organometallic compounds are generally now only used in fuels in small amounts, if at all, as they can be toxic, damaging to the engine and damaging to the environment.

Octane improvers which are not based on metals include oxygenates (e.g. ethers and alcohols) and aromatic amines. However, these additives also suffer from various drawbacks. For instance, N-methyl aniline (NMA), an aromatic amine, must be used at a relatively high treat rate (1.5 to 2% weight additive/weight base fuel) to have a significant effect on the octane number of the fuel. NMA can also be toxic. Oxygenates give a reduction in energy density in the fuel and, as with NMA, have to be added at high treat rates, potentially causing compatibility problems with fuel storage, fuel lines, seals and other engine components.

Recently, a new class of octane-boosting additive has been discovered. These octane-boosting additives are derivatives of benzo[1,4]oxazines and 1,5-benzoxazepines, and show great promise due to their non-metallic nature, their low oxygenate content, and their efficacy at low treat rates (see WO 2017/137518).

Synthesis routes currently reported in the literature provide various descriptions of how benzoxazines could be prepared on a relatively small scale (hundreds of mg to up to 100 kg scale). For example, US 2008/064871—which relates to compounds for the treatment or prophylaxis of diseases relating to uric acid, such as gout—discloses the preparation of benzoxazine-derived compounds.

However, such synthesis methods are not viable for preparing the new class of octane-boosting additives on an industrial scale, e.g. from 50 to up to 20,000 tonnes per year, due to the high cost of specialised raw materials, e.g. methylaminophenols, and reagents, e.g. lithium aluminium hydride and dibromoethane, which are required in stoichiometric amounts.

Accordingly, there is a need for methods for synthesising the new class of octane-boosting additives that may be implemented on a large scale, and which mitigate at least some of the problems highlighted above e.g. by avoiding the use of costly aminophenol starting materials.

SUMMARY OF THE INVENTION

Accordingly, the present invention provides a method for preparing a fuel additive d having the formula:

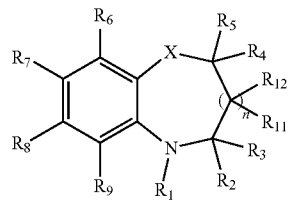

where: $R_1$ is hydrogen;
$R_2$, $R_3$, $R_4$, $R_5$, $R_{11}$ and $R_{12}$ are each independently selected from hydrogen, alkyl, alkoxy, alkoxy-alkyl, secondary amine and tertiary amine groups;
$R_6$, $R_8$ and $R_9$ are each independently selected from hydrogen, alkyl, alkoxy, alkoxy-alkyl, secondary amine and tertiary amine groups;
$R_7$ is selected from alkyl, alkoxy, alkoxy-alkyl, secondary amine and tertiary amine groups;
X is selected from —O— or —$NR_{10}$—, where $R_{10}$ is selected from hydrogen and alkyl groups; and
n is 0 or 1.

The method comprises carrying out the following reaction:

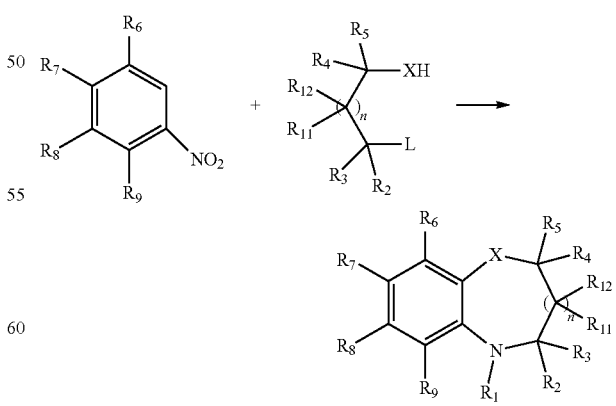

where: L is a leaving group.

Also provided is a fuel additive d which is obtainable by a method of the present invention.

The present invention further provides a process for preparing a fuel for a spark-ignition internal combustion engine, said process comprising:

preparing a fuel additive d using a method of the present invention; and blending the fuel additive with a base fuel.

A fuel for a spark-ignition internal combustion engine is also provided. The fuel comprises a fuel additive d of the present invention and a base fuel.

DETAILED DESCRIPTION OF THE INVENTION

The present invention provides a method for preparing a fuel additive d. According to this method, the fuel additive d is prepared by carrying out the following reaction:

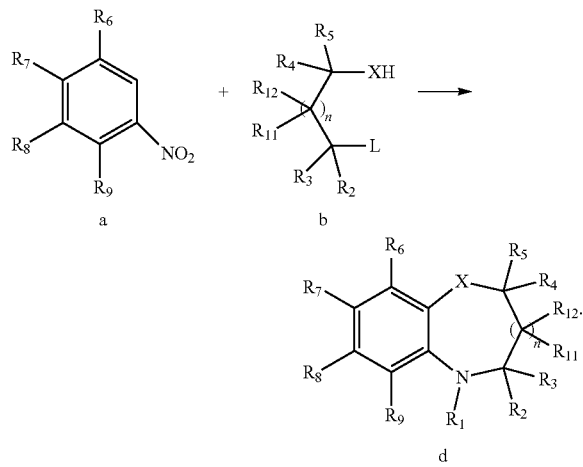

Reagent b may be used in an amount of from 0.8 to 6 molar equivalents, preferably from 0.9 to 4 molar equivalents, and more preferably from 1 to 2.5 molar equivalents as compared to starting material a.

In some embodiments, the reaction is carried out in a single step (i.e. with one set of reagents and under one set of conditions). However, in preferred embodiments, the reaction comprises the following steps:

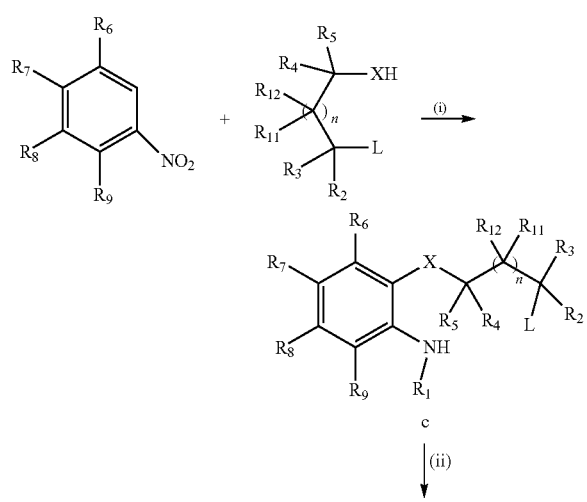

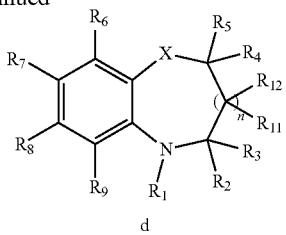

Step (i) of the method is preferably carried out in the presence of a reducing agent. Without wishing to be bound by theory, it is believed that the nitro group of the starting material is partially reduced to form a hydroxylamine intermediate:

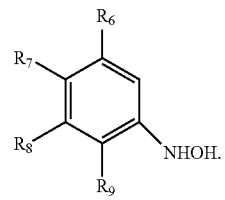

This hydroxylamine intermediate is believed to then react with reagent b to form intermediate c.

The reducing agent may be selected from hydrogen and hydrazine. The reducing agent is used in the presence of a hydrogenation catalyst.

The hydrogenation catalyst is preferably selected from metal catalyst such as palladium (including mixed palladium-ruthenium catalysts), platinum, nickel (e.g. Raney nickel), copper (e.g. Raney copper), zinc, magnesium, rhodium and molybdenum catalysts, though tellurium and selenium catalysts may also be used. The catalysts may be supported, e.g. on carbon, or unsupported. Preferred catalyst are selected from palladium and platinum catalysts, such as from Pd/C, Pt(OH)$_2$, PtS, and PtO$_2$, with Pd/C particularly preferred.

The hydrogenation catalyst may be used in an amount of less than 1 molar equivalent, preferably less than 0.5 molar equivalents, and more preferably less than 0.1 molar equivalents as compared to starting material a.

Hydrogen may be present in step (i) at a pressure of from 0.1 to 20 bar, preferably from 0.5 to 15 bar, and more preferably from 1 to 10 bar hydrogen pressure.

Other reducing agents that may be used, optionally with a catalyst (such as those mentioned above), include borohydrides, such as sodium borohydride, and ammonium chloride.

Step (i) is preferably carried out in the presence of an acid. The acid may be selected from organic acids (e.g. from methanesulfonic acid, acetic acid and p-toluenesulfonic acid) and inorganic acids (e.g. from sulfuric acid, phosphoric acid and ammonium hydrogen sulfate). The acid may be in the form of an aqueous solution.

A molar excess of acid (as compared to starting material a) is preferably used in step (i). For instance, the acid may be used in an amount of greater than 1.5 molar equivalents, preferably greater than 2 molar equivalents, and more preferably greater than 5 molar equivalents as compared to starting material a.

A phase-transfer catalyst may also be used during the reaction. Suitable phase-transfer catalysts include quaternary ammonium salts (e.g. tetraalkylammonium halides, such as butyltriethylammonium chloride or methyltributylammonium chloride) and amine-containing compounds (e.g. tri-alkyl ammonium compounds, such as N,N-dimethyldodecylamine). The amine-containing compounds may convert into a quaternary cationic form in an acidic solution.

The phase-transfer catalyst may be used in an amount of less than 1 molar equivalent, preferably less than 0.5 molar equivalents, and more preferably less than 0.1 molar equivalents as compared to starting material a.

Step (i) may be carried out in a solvent selected from protic solvents, and preferably selected from water, alcohols (e.g. methanol, ethanol or alkylene glycols, preferably with the formula: HO—C($R_1$)($R_2$)[C($R_{11}$)($R_{12}$)]$_n$C($R_4$)($R_5$)—OH, i.e. the alcohol corresponding to reagent b), and organic acids (e.g. acetic acid). Protic solvents are well-known in the art as solvents which are capable of donating protons. Protic solvents contain hydrogen atoms bound to a nitrogen or an oxygen. It will be appreciated that acetic acid may function as both the acid and the solvent in step (i) of the reaction. Preferred solvents include water and the alkylene glycols corresponding to reagent b.

Step (i) may be carried out at a temperature of from 15° C. to 120° C., preferably from 40° C. to 110° C., and more preferably from 50° C. to 100° C.

Step (i) may be conducted at ambient pressure, i.e. approximately 1 bar, though it may also be conducted at elevated pressures, e.g. where greater than 1 bar hydrogen pressure is used.

Step (i) may be conducted for a period of at least 1 hour, preferably at least 4 hours, but preferably less than 24 hours.

In step (ii) of the method, intermediate c is subjected to a ring closing reaction to form fuel additive d:

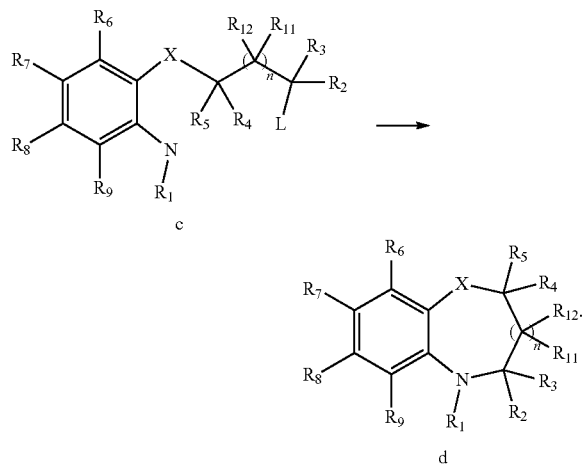

Step (ii) of the method may be conducted in the presence of a hydrogen halide, preferably hydrogen bromide or hydrogen chloride. This is particularly preferred where a hydroxy group is present in intermediate c. The hydrogen halide is preferably in the form of an aqueous solution, e.g. containing greater than 20%, preferably greater than 40% and preferably greater than 50% by weight of the hydrogen halide.

A molar excess of hydrogen halide is preferably used, for instance by using hydrogen halide in an amount of at least 5 molar equivalents, preferably at least 10 molar equivalents, and more preferably at least 15 molar equivalents as compared to intermediate c.

In these embodiments, step (ii) may be conducted at a temperature of greater than 60° C., preferably greater than 70° C., and more preferably greater than 80° C.

In these embodiments, step (ii) may be conducted at ambient pressure, i.e. approximately 1 bar.

The reaction with the hydrogen halide may be conducted for a period of greater than 1 hour, preferably greater than 2 hours, but preferably less than 5 hours.

The reaction with the hydrogen halide in step (ii) is preferably quenched using a base, for instance using an inorganic base such as an alkali metal hydroxide (e.g. sodium hydroxide or potassium hydroxide) or aqueous ammonia.

Alternatively, step (ii) may be conducted in the presence of a thionyl halide, a phosphorus tetrahalide, a phosphorus pentahalide, a phosphoryl halide, or halogen gas (i.e. $Br_2$, $Cl_2$, etc.) or a carbon tetrahalide in combination with a trialkylphosphine (e.g. trimethyl phosphine) or a triaryl phosphine (e.g. triphenyl phosphine). In these embodiments, the halogenation reaction is preferably conducted in the presence of an aprotic solvent (e.g. tetrahydrofuran, acetonitrile, dimethoxyethane, dioxane, N-methyl-2-pyrrolidone, dimethylformamide, dimethylacetamide, dimethyl sulfoxide, ethylene carbonate, sulfolane, diphenyl ether, acetonitrile, 2-nitropropane, acetone, butan-2-one, butylformate, ethyl acetate, isobutyronitrile, methylacetate, methyformate, nitromethane, oxolane or propionitrile, and preferably a non-ether aprotic solvent, such as dimethyl formamide, N-methyl-2-pyrrolidone, dimethylformamide, dimethylacetamide, dimethyl sulfoxide, acetone, dioxane, ethylene carbonate and acetonitrile) or a chlorinated solvent (e.g. dichloromethane, dichloroethylene or trichloromethane).

For instance, the reaction may be carried out using: a thionyl halide, in the presence of a chlorinated solvent (e.g. dichloromethane, dichloroethylene or trichloromethane); a halogen gas or carbon tetrahalide in the presence of a triaryl phosphine (e.g. triphenyl phosphine) or trialkyl phosphine and preferrably an aprotic solvent (e.g. acetonitrile) or a chlorinated solvent (e.g. dichloromethane); a phosphorus trihalide, a phosphorus pentahalide or a phosphoryl halide, preferably in the presence of an ammonium salt (e.g. tetraalkylammonium halides such as tetrabutylammonium bromide); or an alkyl- or aryl-sulfonyl chloride (e.g. toluenesulfonyl chloride or methanesulfonyl chloride), preferably in the presence of a trialkylamine (e.g. trimethyl amine), and preferably in the presence of a chlorinated solvent (e.g. dichloromethane).

As a further alternative, step (ii) may be earned out in the presence of HalOSO$_2$A or ASO$_2$—O—SO$_2$A, where Hal is a halogen (preferably selected from Cl and Br) and A is selected from tolyl, methyl, —CF$_3$, —CH$_2$Cl, phenyl and p-nitrophenyl. The reaction may be conducted in the presence of an aprotic solvent (e.g. tetrahydrofuran, acetonitrile, dimethoxyethane, dioxane, N-methyl-2-pyrrolidone, dimethylformamide, dimethylacetamide, dimethyl sulfoxide, ethylene carbonate, sulfolane, diphenyl ether, acetonitrile, 2-nitropropane, acetone, butan-2-one, butylformate, ethyl acetate, isobutyronitrile, methylacetate, methyformate, nitromethane, oxolane or propionitrile, and preferably a non-ether aprotic solvent, such as dimethyl formamide, N-methyl-2-pyrrolidone, dimethylformamide, dimethylacetamide, dimethyl sulfoxide, acetone, dioxane, ethylene carbonate or acetonitrile, and preferably dimethyl formamide, N-methyl-2-pyrrolidone, dimethylformamide, dimethylacetamide, dimethyl sulfoxide, acetone, dioxane, ethylene carbonate or acetonitrile) or a chlorinated solvent (e.g. dichloromethane, dichloroethylene or trichloromethane).

In other embodiments, step (ii) may be conducted in the presence of a metal catalyst. It will be appreciated that metal catalysts are metal-containing catalysts and, as such, they may contain non-metallic elements.

Suitable metal catalysts include those selected from palladium (e.g. Pd/C, PdO, Pd/Al$_2$O$_3$, Pd/C/ZnO or PdCl$_2$(PPh$_3$)$_2$), nickel (e.g. in the presence of aluminium such as in Raney nickel or Ni—SiO$_2$/Al$_2$O$_3$), cobalt (e.g. in the presence of aluminium such as in Raney cobalt), platinum (e.g. Pt/C, PtO$_2$, Pt/Al$_2$O$_3$, Pt/C/Cu, Pt/C/Fe, PtSiO$_2$ or Pt/C/V), ruthenium (e.g. Ru/C, RuO$_2$, Ru/Al$_2$O$_3$, RuCl$_2$(PPh$_3$)$_3$, Cp*RuCl(PPh$_3$)$_2$, Cp*RuCl(COD), (Cp*RuCl)$_4$ or CpRuCl(PPh$_3$)$_2$), iridium (e.g. Ir/C or [Cp*IrCl$_2$]$_2$), rhodium (e.g. Rh/C, Rh$_2$O$_3$, Rh/Al$_2$O$_3$, [Rh(COD)Cl]$_2$, (PPh$_3$)$_3$RhCl or RhCl(CO)(PPh$_3$)$_2$) and copper (e.g. in the presence of aluminium such as in Raney Cu, CuO/ZnO, CuO/Al$_2$O$_3$/MnO or Cu$_2$Cr$_2$O$_5$) catalysts. As is standard in the art, Cp* represents the ligand 1,2,3,4,5-pentamethylcyclopentadienyl, Cp represents the ligand cyclopentadienyl and COD represents the ligand 1,5-cyclooctadiene.

In these embodiments, the metal catalyst may be used in an amount of up to 0.5 molar equivalents as compared to intermediate c, for instance from 0.001 to 0.5, preferably from 0.005 to 0.4, and more preferably from 0.01 to 0.3 equivalents as compared to intermediate c.

In these embodiments, the reaction is preferably carried out at a temperature of at least 100° C., such as a temperature of from 100 to 250° C.

The reaction in the presence of a metal catalyst in step (ii) may be carried out in the presence of: (1) a basic catalyst; (2) no further reaction components; (3) a hydrogen source, or (4) a reaction additive. Each of these options is described in greater detail below:

(1) Basic Catalyst

Particularly suitable metal catalysts where a basic catalyst is used include ruthenium (e.g. in the form of RuCl$_2$(PPh$_3$)$_3$) and iridium (e.g. [Cp*IrCl$_2$]$_2$) catalysts.

Preferred basic catalysts include inorganic bases, such as those selected from alkali metal carbonates (e.g. alkali metal carbonates such as sodium carbonate, sodium bicarbonate, potassium carbonate and potassium bicarbonate) and alkali metal alkoxides (e.g. alkali metal tert-butoxides such as sodium tert-butoxide or potassium tert-butoxide). Alkali metal oxides are believed to give very high yields.

The base may be used in an amount of from 0.005 to 0.5 molar equivalents, preferably from 0.01 to 0.3 molar equivalents, and more preferably from 0.05 to 0.2 molar equivalents as compared to intermediate c.

The reaction may be carried out in the presence of a solvent system, such as an aprotic solvent system. It will be appreciated that trace amounts (e.g. less than 5%, less than 3% or less than 1% by volume of the aprotic solvent system) of protic solvents may be present, e.g. as a result of the catalyst or base being prepared in a protic solvent such as water.

The aprotic solvent system preferably comprises an aromatic solvent (e.g. a solvent selected from toluene, benzene, xylenes, trimethyl benzenes such as mesitylene, diphenyl ether, naphthalene, methyl-substituted naphthalenes (i.e. 1- or 2-methylnaphthalene) and anisole). The aromatic solvent may be present in the aprotic solvent system in an amount of at least 30%, preferably at least 40%, and more preferably at least 50%, by weight. In embodiments, the aromatic solvent may the only solvent that is used, i.e. the aprotic solvent system consists of the aromatic solvent.

The reaction will generally be carried out substantially in the absence of hydrogen gas, e.g. at a level of less than 10 ppm and preferably less than 1 ppm by volume. Preferably, no further reaction materials (e.g. reagents or catalysts) beyond intermediate c, the metal catalyst, the basic catalyst and, optionally, the solvent system are present.

The reaction is preferably carried out at a temperature of from 100 to 200° C., preferably from 100 to 180° C., and more preferably from 100 to 150° C.

The reaction will generally be carried out at ambient pressure, i.e. at a pressure of approximately 1 bar.

The reaction may be conducted for a period of greater than 2 hours, preferably greater than 12 hours. Typically, the reaction will be carried out for up to 48 hours.

(2) No Further Components

In some particularly preferred embodiments, step (ii) may be carried out in the presence of a metal catalyst and, optionally, a solvent system.

The reaction will generally be carried out substantially in the absence of hydrogen gas, e.g. at a level of less than 10 ppm and preferably less than 1 ppm by volume. Preferably, no further reaction materials (e.g. reagents or catalysts) beyond intermediate c, the metal catalyst and, optionally, the solvent system are present.

Suitable metal catalysts include ruthenium (e.g. as RuCl$_2$(PPh$_3$)$_3$, Cp*RuCl(PPh$_3$)$_2$, Cp*RuCl (COD), (Cp*RuCl)$_4$ or CpRuCl(PPh$_3$)$_2$), palladium (e.g. PdCl$_2$(PPh$_3$)$_2$), rhodium (e.g. [Rh(COD)Cl]$_2$, (PPh$_3$)$_3$RhCl or RhCl(CO)(PPh$_3$)$_2$) and nickel (e.g. Raney nickel) catalysts. Nickel catalysts are believed to be particularly suitable, with Raney nickel in particular providing a high yield.

The reaction is optionally carried out in the presence of a solvent system. However, in some embodiments, it is preferred to carry out the reaction using solely intermediate c as the solvent. This system is chemically very efficient and is capable of producing the compound d in large yields.

Solvent systems that may be used include aprotic solvent systems. It will be appreciated that trace amounts (e.g. less than 5%, less than 3% or less than 1% by volume of the aprotic solvent system) of protic solvents may be present during the reaction, e.g. as a result of the catalyst being prepared as a catalyst-in-water slurry.

The aprotic solvent system preferably may comprise an aromatic solvent, such as a solvent selected from toluene, benzene, xylenes, trimethyl benzenes such as mesitylene, diphenyl ether, naphthalene, methyl-substituted naphthalenes and anisole. Mesitylene is particularly suitable, delivering high yields of the compound d.

The aromatic solvent may be present in the aprotic solvent system in an amount of at least 30%, preferably at least 40%, and more preferably at least 50%, by weight. In preferred embodiments, the aromatic solvent may the only solvent that is used, i.e. the aprotic solvent system consists of the aromatic solvent.

The aprotic solvent system may comprise a non-aromatic solvent. Preferred non-aromatic solvents are selected from heterocyclic solvents, such as from N-methyl-2-pyrrolidone, tetrahydrofuran and 1,4-dioxane. Other suitable aprotic non-aromatic solvents include dimethylacetamide. The non-aromatic solvent may be used alone or in combination with an aromatic solvent.

The solvent system may be used in an amount of up to 10 volume equivalents, for instance from 1 to 10 volume equivalents, preferably from 1.5 to 5 volume equivalents, and more preferably from 2 to 3 volume equivalents, as compared to intermediate c.

The reaction is preferably carried out at a temperature of from 100 to 200° C., preferably from 115 to 180° C., and more preferably from 130 to 160° C.

The reaction will generally be carried out at ambient pressure, i.e. at a pressure of approximately 1 bar.

The reaction may be conducted for a period of greater than 2 hours, preferably greater than 10 hours, for instance greater than 20. Typically, the reaction will be carried out for up to 30 hours. These values represent the period of time over which the reaction is out at a temperature of at least 100° C.

(3) Hydrogen Source

In some preferred embodiments, step (ii) may be carried out in the presence of a metal catalyst, a hydrogen source and an aprotic solvent system.

The reaction may be carried out in the presence of a wide range of metal catalysts. Suitable metal catalysts include those selected from palladium (e.g. Pd/C, PdO, Pd/Al$_2$O$_3$, Pd/C/ZnO or PdCl$_2$(PPh$_3$)$_2$), nickel (e.g. in the presence of aluminium such as in Raney nickel or Ni—SiO$_2$/Al$_2$O$_3$), cobalt (e.g. in the presence of aluminium such as in Raney cobalt), platinum (e.g. Pt/C, Pt/Al$_2$O$_3$, Pt/C/Cu, Pt/C/Fe, PtSiO$_2$ or Pt/CN), ruthenium (e.g. Ru/C or Ru/Al$_2$O$_3$), iridium (e.g. Ir/C), rhodium (e.g. Rh/C, Rh/Al$_2$O$_3$, [Rh(COD)Cl]$_2$, (PPh$_3$)$_3$RhCl or RhCl(CO)(PPh$_3$)$_2$), copper (e.g. in the presence of aluminium such as in Raney Cu, CuO/ZnO, CuO/Al$_2$O$_3$/MnO or Cu$_2$Cr$_2$O$_5$) and ruthenium (e.g. Cp*RuCl(PPh$_3$)$_2$, Cp*RuCl(COD), (Cp*RuCl)$_4$ or CpRuCl(PPh$_3$)$_2$) catalysts. Nickel catalysts, in particular Ni—SiO$_2$/Al$_2$O$_3$, are particularly suitable since these catalysts are believed to give high yields of the compound d.

The reaction is preferably carried out as a heterogeneous catalyst reaction. Heterogeneous catalysis reactions involve the use of a catalyst in a different phase from the reactants. In this embodiment, the reaction is preferably carried out with a solid catalyst in a liquid reagent phase. Thus, preferred metal catalysts are supported, e.g. on insoluble media, such as on carbon, alumina or silica. The metal catalyst may be used in the form of a slurry or in the form of a fixed bed catalyst.

The reaction is carried out in the presence of a hydrogen source. The hydrogen source is preferably hydrogen gas, for instance at a pressure of from 1 to 50 bar, preferably from 3 to 30 bar, and more preferably from 5 to 15 bar. Though less preferred, hydrogen transfer reagents could also be used as the hydrogen source, e.g. formic acid, sodium formate or ammonium formate.

The reaction is carried out in the presence of an aprotic solvent system. It will be appreciated that trace amounts (e.g. less than 5%, less than 3% or less than 1% by volume of the aprotic solvent system) of protic solvents may be present during the reaction, e.g. as a result of the catalyst being prepared as a catalyst-in-water slurry.

The aprotic solvent system preferably comprises an aromatic solvent, such as a solvent selected from toluene, benzene, xylenes, trimethyl benzenes such as mesitylene, diphenyl ether, naphthalene, methyl-substituted naphthalenes and anisole. Mesitylene is particularly suitable, delivering high yields of the compound d.

The aromatic solvent may be present in the aprotic solvent system in an amount of at least 30%, preferably at least 40%, and more preferably at least 50%, by weight. In embodiments, the aromatic solvent may the only solvent that is used, i.e. the aprotic solvent system consists of the aromatic solvent.

The aprotic solvent system may also comprise a non-aromatic solvent. Preferred non-aromatic solvents are selected from heterocyclic solvents, such as from N-methyl-2-pyrrolidone, tetrahydrofuran and 1,4-dioxane. Other suitable aprotic non-aromatic solvents include dimethylacetamide. The non-aromatic solvent is preferably used in combination with an aromatic solvent.

Preferably, no further reaction materials (e.g. reagents or catalysts) beyond intermediate c, the metal catalyst, the hydrogen source and, optionally, the aprotic solvent system are present.

The reaction is preferably carried out at a temperature of at a temperature of from 100 to 250° C., preferably from 130 to 230° C., and more preferably from 150 to 200° C.

The reaction will generally be carried out at just one temperature. However, in some embodiments, the reaction may be brought up to temperature over a period of up to 3 hours, preferably up to 2 hours, and more preferably up to 1.5 hours. For instance, the reaction may be carried out at a temperature of from 40 to 100° C. for a period of to 3 hours, preferably up to 2 hours, and more preferably up to 1.5 hours, before the reaction is taken up to full temperature.

The reaction may be conducted for a period of greater than 2 hours, preferably greater than 4 hours. Typically, the reaction will be carried out for up to 24 hours. These values represent the period of time over which the reaction is out at a temperature of at least 100° C.

(4) Reaction Additive

In some embodiments, step (ii) may be carried out in the presence of a metal catalyst and a reaction additive.

Suitable metal catalysts include those selected from palladium (e.g. Pd/C or PdO), platinum (e.g. Pt/C or PtO$_2$), ruthenium (e.g. Ru/C or RuO$_2$) and rhodium (e.g. Rh/C or Rh$_2$O$_3$) catalysts. Palladium catalysts are particularly suitable, since they are believed to give the compound d in high yields.

The reaction is carried out in the presence of a reaction additive. Suitable reaction additives include metal oxides and inorganic basis. Preferred metal oxides include zinc oxide. Preferred inorganic bases include such as alkali metal hydroxides, alkali metal carbonates (including alkali metal hydrogen carbonates), alkali metal phosphates and alkali metal formates. Sodium or potassium will typically be used as the alkali metal. Preferred inorganic bases include sodium formate. Metal oxides such as zinc oxide are preferred when an aqueous solvent system is used, whereas alkali metal bases such as sodium formate are preferred for use with aprotic solvent systems.

The reaction additive may be used in an amount of up to 5 molar equivalents, for instance from 0.1 to 5 molar equivalents, preferably from 0.5 to 4 molar equivalents, and more preferably from 1 to 3 molar equivalents, as compared to intermediate c. It will be appreciated that the reaction additive may be used in over-stoichiometric amounts and will typically be consumed in the reaction as a reagent.

The reaction may be carried out in the presence of a protic or an aprotic solvent system, though aprotic solvent systems are generally preferred. It will be appreciated that trace amounts (e.g. less than 5%, less than 3% or less than 1% by volume of the aprotic solvent system) of protic solvents may be present during the reaction, e.g. as a result of the catalyst or reaction additive being prepared in a protic solvent such as water.

Protic solvents are well-known in the art as solvents which are capable of donating protons. Protic solvents typically contain hydrogen atoms directly bound to a nitrogen or an oxygen.

Protic solvent systems include aqueous, i.e. water-containing, solvent systems. In some embodiments, the aqueous solvent system may contain only water. In other embodiments, a mixture of water and an alcohol (e.g. tert-butanol) or ether (e.g. dimethoxyethane) may be used.

Suitable aprotic solvent systems preferably comprise an aromatic solvent (e.g. a solvent selected from toluene, benzene, xylenes, trimethyl benzenes such as mesitylene, diphenyl ether, naphthalene, methyl-substituted naphthalenes and anisole) or a non-aromatic solvent (e.g. N-methyl-2-pyrrolidone, tetrahydrofuran and 1,4-dioxane).

In some embodiments, an aromatic aprotic solvent, e.g. as described above, may be used in combination with a protic solvent, e.g. as described above. Toluene and tert-butanol may be used together.

The reaction will generally be carried out substantially in the absence of hydrogen gas, e.g. at a level of less than 10 ppm and preferably less than 1 ppm by volume. Preferably, no further reaction materials (e.g. reagents or catalysts) beyond intermediate c, the metal catalyst, the reaction additive and, optionally, the solvent system are present.

The reaction is preferably carried out at a temperature of at a temperature of from 105 to 200° C., preferably from 110 to 180° C., and more preferably from 120 to 160° C. The reaction will generally be carried out at just one temperature.

The reaction will generally be carried out at ambient pressure, i.e. at a pressure of approximately 1 bar.

The reaction may be conducted for a period of greater than 6 hours, preferably greater than 12 hours. Typically, the reaction will be carried out for up to 136 hours.

These values represent the period of time over which the reaction is out at a temperature of at least 100° C.

Leaving group L is lost during step (ii). L is preferably selected from halides (e.g. Cl, Br, I), substituted aryloxy groups (e.g. —O—Ar, where Ar is selected from nitro-substituted aryl groups such as p-nitrophenyl), sulfonates (e.g. —OSO$_2$A, where A is selected from tolyl, methyl, —CF$_3$, —CH$_2$Cl, phenyl and p-nitrophenyl) and —XH. L is preferably selected from Cl, Br and —XH, and more preferably is —XH.

The methods of the present invention are preferably carried out on an industrial scale. For instance, where the method of preparing fuel additive d is a batch process, the fuel additive is preferably produced in a batch quantity of greater than 100 kg, preferably greater than 150 kg, and more preferably greater than 200 kg of fuel additive. The method may also be carried out as a continuous process.

In order to produce the fuel additive d on an industrial scale, the reaction is preferably carried out in a reactor or, where the reaction comprises steps (i) and (ii), reactors having a capacity of at least 500 L, preferably at least 750 L, and more preferably at least 1000 L. It will be appreciated that, where the reaction comprises steps, both steps (i) and (ii) may be carried out in the same reactor.

Octane-Boosting Fuel Additive

Fuel additives d that are prepared using the methods of the present invention have the following formula:

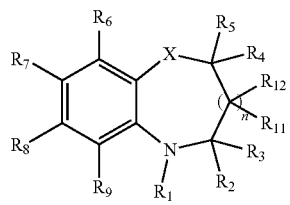

where: $R_1$ is hydrogen;
$R_2$, $R_3$, $R_4$, $R_5$, $R_{11}$ and $R_{12}$ are each independently selected from hydrogen, alkyl, alkoxy, alkoxy-alkyl, secondary amine and tertiary amine groups;
$R_6$, $R_8$ and $R_9$ are each independently selected from hydrogen, alkyl, alkoxy, alkoxy-alkyl, secondary amine and tertiary amine groups;
$R_7$ is selected from alkyl, alkoxy, alkoxy-alkyl, secondary amine and tertiary amine groups;
X is selected from —O— or —NR$_{10}$—, where $R_{10}$ is selected from hydrogen and alkyl groups; and
n is 0 or 1.

Preferred substituents for the fuel additives are described below. It will be appreciated that the preferred substitution patterns also apply to the starting material a, reagent b, and intermediate c from which the fuel additive d is prepared.

In some embodiments, $R_2$, $R_3$, $R_4$, $R_5$, $R_{11}$ and $R_{12}$ are each independently selected from hydrogen and alkyl groups, and preferably from hydrogen, methyl, ethyl, propyl and butyl groups. More preferably, $R_2$, $R_3$, $R_4$, $R_5$, $R_{11}$ and $R_{12}$ are each independently selected from hydrogen, methyl and ethyl, and even more preferably from hydrogen and methyl.

In some embodiments, $R_6$, $R_8$ and $R_9$ are each independently selected from hydrogen, alkyl and alkoxy groups, and preferably from hydrogen, methyl, ethyl, propyl, butyl, methoxy, ethoxy and propoxy groups. More preferably, $R_6$, $R_7$, $R_8$ and $R_9$ are each independently selected from hydrogen, methyl, ethyl and methoxy, and even more preferably from hydrogen, methyl and methoxy.

In some embodiments, $R_7$ is selected from alkyl and alkoxy groups, and preferably from methyl, ethyl, propyl, butyl, methoxy, ethoxy and propoxy groups. More preferably, $R_7$ is selected from methyl, ethyl and methoxy, and even more preferably from methyl and methoxy. It is believed that the presence of at least one group other than hydrogen may improve the solubility of the octane-boosting additives in a fuel.

Advantageously, no more than five, preferably no more than three, and more preferably no more than two, of $R_2$, $R_3$, $R_4$, $R_5$, $R_6$, $R_7$, $R_8$, $R_9$, $R_{11}$ and $R_{12}$ are selected from a group other than hydrogen. Preferably, one or two of $R_2$, $R_3$, $R_4$, $R_5$, $R_6$, $R_7$, $R_8$, $R_9$, $R_{11}$ and $R_{12}$ are selected from a group other than hydrogen. In some embodiments, only $R_7$ is selected from a group other than hydrogen.

It is also preferred that at least one of $R_2$ and $R_3$ is hydrogen, and more preferred that both of $R_2$ and $R_3$ are hydrogen.

In preferred embodiments, $R_7$ and optionally $R_4$, $R_5$, and $R_8$ are selected from methyl, ethyl, propyl and butyl groups and the remainder of $R_2$, $R_3$, $R_4$, $R_5$, $R_6$, $R_8$, $R_9$, $R_{11}$ and $R_{12}$ are hydrogen. More preferably, $R_7$ and optionally $R_8$ are selected from methyl, ethyl, propyl and butyl groups and the remainder of $R_2$, $R_3$, $R_4$, $R_5$, $R_6$, $R_8$, $R_9$, $R_{11}$ and $R_{12}$ are hydrogen.

In further preferred embodiments, $R_7$ and optionally $R_4$, $R_5$, and $R_8$ are methyl groups and the remainder of $R_2$, $R_3$, $R_4$, $R_5$, $R_6$, $R_8$, $R_9$, $R_{11}$ and $R_{12}$ are hydrogen. More preferably, $R_7$ and optionally $R_8$ are methyl groups and the remainder of $R_2$, $R_3$, $R_4$, $R_5$, $R_6$, $R_8$, $R_9$, $R_{11}$ and $R_{12}$ are hydrogen.

Preferably, X is —O— or —NR$_{10}$—, where $R_{10}$ is selected from hydrogen, methyl, ethyl, propyl and butyl groups, and preferably from hydrogen, methyl and ethyl groups. More preferably, $R_{10}$ is hydrogen. In preferred embodiments, X is —O—.

n may be 0 or 1, though it is preferred that n is 0.

Octane-boosting additives that may be used in the present invention include:

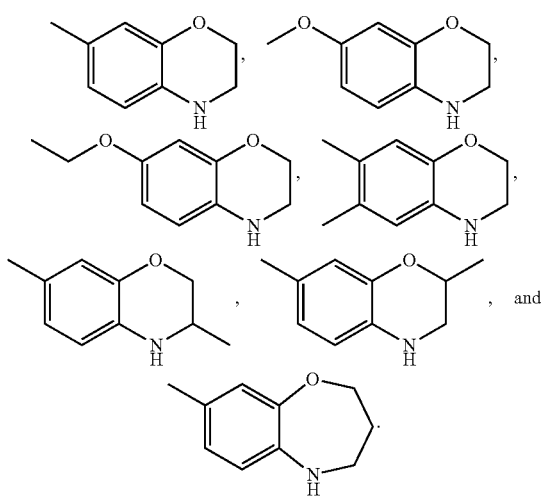

Preferred octane-boosting additives include:

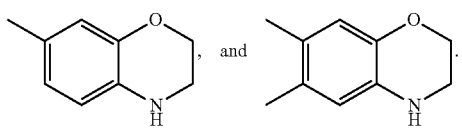

Particularly preferred is the octane-boosting additive:

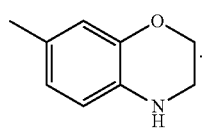

A mixture of additives may be used in the fuel composition. For instance, the fuel composition may comprise a mixture of:

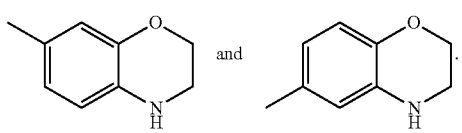

It will be appreciated that references to alkyl groups include different isomers of the alkyl group. For instance, references to propyl groups embrace n-propyl and i-propyl groups, and references to butyl embrace n-butyl, isobutyl, sec-butyl and tert-butyl groups.

Additive and Fuel Compositions

The present invention provides fuel additives d which are obtainable by a method of the present invention. Preferably, the fuel additives are obtained by a method of the present invention.

The present invention also provides a process for preparing a fuel for a spark-ignition internal combustion engine, said process comprising:

preparing a fuel additive d using a method of the present invention; and blending the fuel additive with a base fuel.

A fuel for a spark-ignition internal combustion engine is also provided. The fuel comprises a fuel additive d, obtainable and preferably obtained by a method of the present invention, and a base fuel.

Gasoline fuels (including those containing oxygenates) are typically used in spark-ignition internal combustion engines. Commensurately, the fuel composition that may be prepared according to the process of the present invention may be a gasoline fuel composition.

The fuel composition may comprise a major amount (i.e. greater than 50% by weight) of liquid fuel ("base fuel") and a minor amount (i.e. less than 50% by weight) of fuel additive composition of the present invention. Examples of suitable liquid fuels include hydrocarbon fuels, oxygenate fuels and combinations thereof.

The fuel composition may contain the octane-boosting fuel additive d in an amount of up to 20%, preferably from 0.1% to 10%, and more preferably from 0.2% to 5% weight additive/weight base fuel. Even more preferably, the fuel composition contains the fuel additive in an amount of from 0.25% to 2%, and even more preferably still from 0.3% to 1% weight additive/weight base fuel. It will be appreciated that, when more than one octane-boosting fuel additive d is used, these values refer to the total amount of octane-boosting additive described herein in the fuel.

The fuel compositions may comprise at least one other further fuel additive. Examples of such other additives that may be present in the fuel compositions include detergents, friction modifiers/anti-wear additives, corrosion inhibitors, combustion modifiers, anti-oxidants, valve seat recession additives, dehazers/demulsifiers, dyes, markers, odorants, anti-static agents, anti-microbial agents, and lubricity improvers. Further octane improvers may also be used in the fuel composition, i.e. octane improvers which do not have the structure of octane-boosting fuel additive d.

The fuel compositions are used in a spark-ignition internal combustion engine. Examples of spark-ignition internal combustion engines include direct injection spark-ignition engines and port fuel injection spark-ignition engines. The spark-ignition internal combustion engine may be used in automotive applications, e.g. in a vehicle such as a passenger car.

The invention will now be described with reference to the following non-limiting examples.

EXAMPLES

Example 1: Preparation of Intermediate C

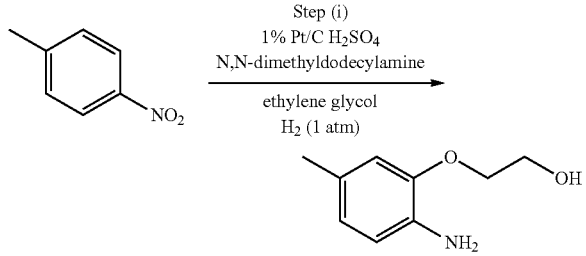

4-nitrotoluene (5.0 g, 36 mmol) and ethylene glycol (4.5 g, 72 mmol) were placed in a flask with 10% w/w aqueous sulfuric acid (30 mL), 1% Pt/C catalyst (20 mg) and N,N-dimethyldodecylamine (0.145 M solution in 10% w/w aqueous sulfuric acid, 0.75 mL). The mixture was exposed to an atmosphere of hydrogen (1 atm) and stirred for 18 hours at 90° C. The reaction mixture was cooled and a sample extracted for analysis by LC-MS to show conversion to the 2-(2-amino-5-methylphenoxy)ethanol product.

Example 2: Preparation of Octane-Boosting Fuel Additive D

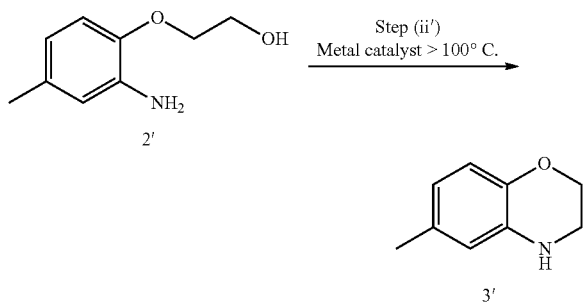

Cyclisation reactions in the presence of a metal catalyst but in the absence of a base, hydrogen or other reaction components were carried out under a variety of conditions. As a general procedure, a mixture of compound 2' and the catalyst were heated, optionally in the presence of a solvent, to the specified temperature. Heating was continued, before cooling to room temperature and sampling for UPLC analysis.

The yields obtained of compound 3' under different conditions are shown in the following table:

| Catalyst | Solvent | Temp (° C.) | Time (hours) | Yield |
|---|---|---|---|---|
| RuCl$_2$(PPh$_3$)$_3$ (1.6 mol %) | none | 145 | 3 | 52% |
| RuCl$_2$(PPh$_3$)$_3$ (2.2 mol %) | NMP | 105 | 3.5 | 3% |
|  |  | 120 | 2 | 5% |
| RuCl$_2$(PPh$_3$)$_3$ (1.7 mol %) | toluene | 105 | 3.5 | 4% |
|  |  | 120 | 2 | 5% |

Further experiments were carried out. As a general procedure, a mixture of compound 2', Raney Ni (50% in water) and mesitylene was heated. The crude reaction mixture was analysed by HPLC to determine conversion and selectivity The yields obtained of compound 3' under different conditions are shown in the following table:

| Solvent volume | Catalyst amount (eq) | Temp (° C.) | Time (h) | Yield |
|---|---|---|---|---|
| None | 0.6 | 150 | 16.5 | 76% |
|  |  |  | >21 | 84% |
| 16 | 0.2 | 167 | 4 | 11% |
| 1.6 | 0.6 | 150 | 21 | 80% |
| 3.2 | 0.8 | 150 | 21 | 83% |
| 3.2 | 0.6 | 150 | 21 | 88% |
| 1.1 | 0.4 | 140 | 16.5 | 73% |
|  |  |  | 40 | 78% |
| 2.3 | 0.4 | 140 | 16.5 | 59% |
|  |  |  | 40 | 77% |
| 1.1 | 0.2 | 140 | 16.5 | 49% |
|  |  |  | 40 | 70% |
| 2.3 | 0.2 | 140 | 16.5 | 67% |
|  |  |  | 40 | 63% |
| 2.4 | 0.4 | 140 | 67 | 90% |
|  |  |  | 91 | 91% |
| 2.4 | 0.2 | 140 | 67 | 86% |
|  |  |  | 91 | 86% |
| 3.4 | 0.2 | 140 | 67 | 88% |
|  |  |  | 91 | 78% |
| 2.4 | 0.2 | 140 | 67 | 90% |
|  |  |  | 91 | 90% |
| 3.4 | 0.2 | 140 | 67 | 88% |
|  |  |  | 91 | 87% |
| 2.5 | 0.2 | 140 | 69 | 84% |
|  |  |  | 93 | 86% |
| 1.5 | 0.2 | 140 | 69 | 81% |
|  |  |  | 93 | 83% |
| 3.5 | 0.2 | 140 | 69 | 78% |
|  |  |  | 93 | 81% |
| 2.5 | 0.2 | 125 | 69 | 56% |
|  |  |  | 93 | 63% |
| 2.5 | 0.3 | 150 | 5.5 | 80% |
|  |  |  | 21.5 | 91% |
|  |  |  | 26.5 | 91% |
| 2.5 | 0.3 | 150 | 5.5 | 75% |
|  |  |  | 21.5 | 94% |
|  |  |  | 26.5 | 95% |

Further experiments were carried out in the presence of a metal catalyst and hydrogen gas. As a general procedure, catalyst was added to an argon flushed stainless steel autoclave (300 mL). To this was added material 2' (0.33 g, 2.0 mmol) followed by mesitylene (10 mL). The autoclave was sealed, charged to 7 bar with hydrogen and heated to 170° C., except in the cases of Experiments xxxii, xxxiii and xxxiv where the temperature was raised to 210° C. The reaction was held at this temperature for 20 hours, before cooling to room temperature and sampling for UPLC (MeCN) analysis.

The yields obtained of compound 3' under different conditions are shown in the following table:

| Entry | Catalyst (amount) | Yield |
|---|---|---|
| i | Raney Ni (slurry in water) | 53% |
| ii | Ni(65% wt)/Al$_2$O$_3$/SiO$_2$ (10 mol %) | 72% |
| iii | Pd/C (5 wt %) | 5% |
| iv | Pt/C (5 wt %) | 6% |
| v | Ru/C (5 wt %) | 55% |
| vi | Pd/Al$_2$O$_3$ (5 wt %) | 9% |

-continued

| Entry | Catalyst (amount) | Yield |
|---|---|---|
| vii | Ru(5% wt)/C (5 wt %) | 80% |
| viii | Pt/C (5 wt %) | 9% |
| ix | Pt/C (5 wt %) | 30% |
| x | Raney Ni (5 wt %) | 75% |
| xi | Raney Ni (5 wt %) | 54% |
| xii | Ni(65% wt)/Al$_2$O$_3$/SiO$_2$ (5 wt %) | 52% |
| xiii | Ni(65 wt %)/Al$_2$O$_3$/SiO$_2$ (10 mol %) | 72% |
| xiv | Ir(5% wt)/C (5 wt %) | 44% |
| xv | Rh(5% wt)/C (5 wt %) | 11% |
| xvi | Raney Co (5 wt %) | 64% |
| xvii | Pt(5% wt)/Al$_2$O$_3$ (5 wt %) | 14% |
| xviii | Pt/Fe/C (5 wt %) | 43% |
| xix | Pt/C/Cu(1% wt) (5 wt %) | 51% |
| xx | Raney Cu (5 wt %) | 2% |
| xxi | Rh (5 wt %)/Al$_2$O$_3$ (5 wt %) | 8% |
| xxii | Pd (5 wt %)/Al$_2$O$_3$ (5 wt %) | 17% |
| xxiii | Pd (5 wt %)/Lindlars (5 wt %) | 59% |
| xxiv | Pt(5 wt %)/Al$_2$O$_3$ (5 wt %) | 31% |
| xxv | Pt/C(5 wt %) (5 wt %) | 14% |
| xxvi | Pt(5 wt %)/SiO$_2$ (5 wt %) | 20% |
| xxvii | CuO/ZnO(50 wt %) (5 wt %) | 5% |
| xxviii | CuO(50 wt %)/Al$_2$O$_3$/MnO (5 wt %) | 12% |
| xxix | Ru(5 wt %)/Al$_2$O$_3$ (5 wt %) | 26% |
| xxx | Pd/C(5 wt %)/ZnO (5 wt %) | 62% |
| xxxi | Pt/C/V(5 wt %) (5 wt %) | 18% |
| xxxii | CuO/ZnO(50 wt %) (5 wt %) | 19% |
| xxxiii | CuO(50 wt %)/Al$_2$O$_3$/MnO (5 wt %) | 17% |
| xxxiv | Cu$_2$Cr$_2$O$_5$ (5 wt %) | 6% |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope and spirit of this invention.

The invention claimed is:

1. A method for preparing a fuel additive having the formula:

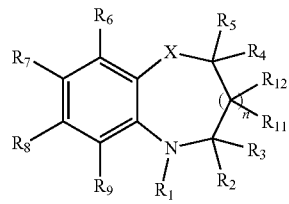

where: $R_1$ is hydrogen;

$R_2$, $R_3$, $R_4$, $R_5$, $R_{11}$ and $R_{12}$ are each independently selected from hydrogen, alkyl, alkoxy, alkoxy-alkyl, secondary amine and tertiary amine groups;

$R_6$, $R_8$ and $R_9$ are each independently selected from hydrogen, alkyl, alkoxy, alkoxy-alkyl, secondary amine and tertiary amine groups;

$R_7$ is selected from alkyl, alkoxy, alkoxy-alkyl, secondary amine and tertiary amine groups;

X is selected from —O— or —NR$_{10}$—, where $R_{10}$ is selected from hydrogen and alkyl groups; and n is 0 or 1, said method comprising carrying out the following reaction:

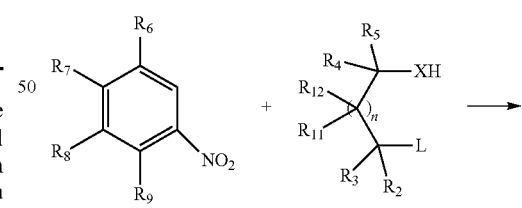

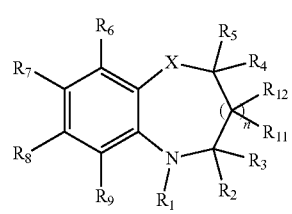

where: L is a leaving group.

2. A method according to claim 1, wherein the reaction comprises the following steps:

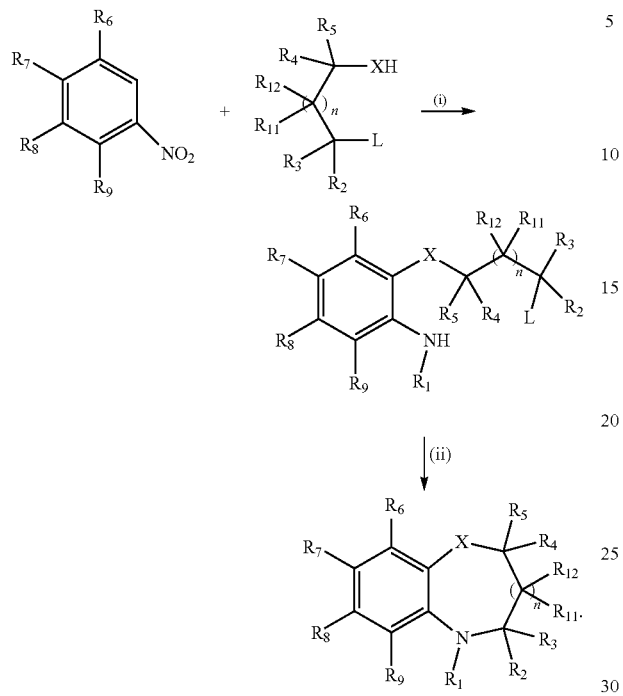

3. A method according to claim 2, wherein step (i) is carried out in the presence of a reducing agent, and wherein the reducing agent is hydrogen or hydrazine, in the presence of a hydrogenation catalyst.

4. A method according to claim 3, wherein the hydrogenation catalyst is selected from palladium, platinum, nickel, copper, zinc, magnesium, rhodium and molybdenum catalysts.

5. A method according to claim 3, wherein the reducing agent is hydrogen in the presence of a hydrogenation catalyst, and wherein hydrogen is present in step (i) at a pressure of from 0.1 to 20 bar hydrogen pressure.

6. A method according to claim 2, wherein step (i) is carried out in the presence of an acid.

7. A method according to claim 2, wherein step (i) is carried out in the presence of a phase-transfer catalyst selected from quaternary ammonium salts and amine-containing compounds.

8. A method according to claim 2, wherein step (i) is carried out in the presence of a solvent selected from protic solvents selected from water, alcohols, and organic acids.

9. A method according to claim 2, wherein step (i) is carried out at a temperature of from 15° C. to 120° C.

10. A method according to claim 2, wherein step (ii) is carried out in the presence of a hydrogen halide.

11. A method according to claim 2, wherein step (ii) is carried out in the presence of a metal catalyst.

12. A method according to claim 11, wherein the metal catalyst is used in an amount of up to 0.5 molar equivalents as compared to intermediate c.

13. A method according to claim 11, wherein the reaction is carried out at a temperature of at least 100° C.

14. A method according to claim 11, wherein the reaction is carried out in the presence of: (1) a basic catalyst; (2) no further reaction components; (3) a hydrogen source, or (4) a reaction additive.

15. A method according to claim 1, wherein L is selected from: halides, substituted aryloxy groups, sulfonates and —XH.

16. A method according to claim 1, wherein the method is a batch process in which the fuel additive is produced in a batch quantity of greater than 100 kg.

17. A method according to claim 1, wherein the method is a continuous process.

18. A process for preparing a fuel for a spark-ignition internal combustion engine, said process comprising:

preparing a fuel additive of the formula:

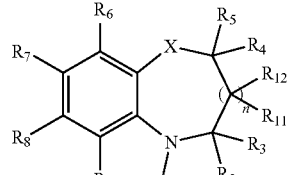

where: $R_1$ is hydrogen;
$R_2$, $R_3$, $R_4$, $R_5$, $R_{11}$ and $R_{12}$ are each independently selected from hydrogen, alkyl, alkoxy, alkoxy-alkyl, secondary amine and tertiary amine groups;
$R_6$, $R_8$ and $R_9$ are each independently selected from hydrogen, alkyl, alkoxy, alkoxy-alkyl, secondary amine and tertiary amine groups;
$R_7$ is selected from alkyl, alkoxy, alkoxy-alkyl, secondary amine and tertiary amine groups;
X is selected from —O— or —$NR_{10}$—, where $R_{10}$ is selected from hydrogen and alkyl groups; and
n is 0 or 1, comprising carrying out the following reaction:

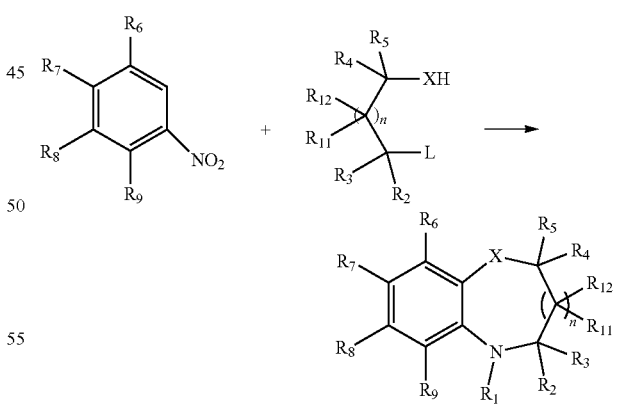

where: L is a leaving group; and
blending the fuel additive with a fuel for a spark-ignition internal combustion engine.

* * * * *